(12) United States Patent
Miller

(10) Patent No.: US 10,912,753 B1
(45) Date of Patent: Feb. 9, 2021

(54) TOPICAL SKIN CARE COMPOSITION

(71) Applicant: Bruce Wayne Miller, Naples, FL (US)

(72) Inventor: Bruce Wayne Miller, Naples, FL (US)

(*) Notice: Subject to any disclaimer, the term of this patent is extended or adjusted under 35 U.S.C. 154(b) by 0 days.

(21) Appl. No.: 17/074,812

(22) Filed: Oct. 20, 2020

(51) Int. Cl.
| | |
|---|---|
| *A61K 36/00* | (2006.01) |
| *A61K 31/245* | (2006.01) |
| *A61K 47/12* | (2006.01) |
| *A61K 47/18* | (2017.01) |
| *A61K 35/644* | (2015.01) |
| *A61K 31/618* | (2006.01) |
| *A61K 47/20* | (2006.01) |
| *A61K 36/61* | (2006.01) |
| *A61K 31/4166* | (2006.01) |
| *A61K 47/02* | (2006.01) |

(52) U.S. Cl.
CPC ........ *A61K 31/245* (2013.01); *A61K 31/4166* (2013.01); *A61K 31/618* (2013.01); *A61K 35/644* (2013.01); *A61K 36/61* (2013.01); *A61K 47/02* (2013.01); *A61K 47/12* (2013.01); *A61K 47/18* (2013.01); *A61K 47/20* (2013.01)

(58) Field of Classification Search
None
See application file for complete search history.

(56) References Cited

FOREIGN PATENT DOCUMENTS

WO    WO-9300114 A1 * 1/1993 ............. A61K 45/06

\* cited by examiner

*Primary Examiner* — Qiuwen Mi
(74) *Attorney, Agent, or Firm* — Tiffany C. Miller; Inventions International Inc.

(57) ABSTRACT

A topical skin care composition for rejuvenation of the skin containing tetracaine, purified water, stearic acid, lauramide diethanolamine, beeswax, propylene glycol, sodium tetraborate, sodium lauryl sulfate, benzyl alcohol, glycerin, diazolidinyl urea, triethanolamine, methyl salicylate, and *eucalyptus* oil. The topical skin care composition of the invention is useful in the healing of the skin and in particular, after the skin has been exfoliated.

7 Claims, No Drawings

TOPICAL SKIN CARE COMPOSITION

BACKGROUND OF THE INVENTION

1. Field of the Invention

This invention relates, generally, to a topical skin care composition having medicinal properties, in particular, it relates to a topical composition for use in post-exfoliation skin care, treating burns, scalds, blisters, rash, scabs or other skin conditions experienced by human and/or animal skin.

2. Background Art

Exfoliation including, but not limited to, a chemical peel, a scrub, microdermabrasion, and/or a topical exfoliant composition removes the outermost surface of an individual's skin in an attempt to reduce visible signs of skin aging, acne, and discoloration. In particular, the exfoliation process occurs during the removal of dead cells in the topmost stratum corneum layer of skin, which in turn stimulates an increase in cell turnover. Thus, brighter and smoother skin is revealed as the outermost surface of an individual's skin flakes and/or peels away. Depending on an individual's skin sensitivity, an individual may feel tingling, burning, itching, dryness, redness, inflammation, or tightness after exfoliation. Proper post-exfoliation skin care products can help minimize many of these aforementioned sensations or visible side effects of exfoliation. For example, moisturizers currently used in today's market are applied to the post-exfoliation site of a user's skin to help hydrate and reinforce the skin's protective barrier that may have been compromised during the exfoliation process. However, many of these skin care products including, moisturizers do not have medicinal properties capable of treating burns, redness, and inflammation associated with post-exfoliated skin. Thus, there is a need for an improved topical skin care composition capable of relaxing and healing the post-exfoliated skin of an individual.

Burns cause inflammation of the skin, pain and swelling and may result in scabbing and scarring. Skin burns are a complex inflammatory process causing dyskeratotic cells, spongiosis, vacuolation of keratinocytes and edema from capillary leakage, 12 to 24 hours after exposure to light or high temperature. In addition to redness and pain, blisters may develop and scabs and scars may result. Known treatments for burns are limited in efficacy. The topical use of anti-inflammatory agents to alleviate inflammation resulting from burns is known. Compositions containing steroidal anti-inflammatories, non-steroidal anti-inflammatories, as well as "natural" anti-inflammatories, such as extract of the plant aloe vera, have been used. In the past there have been many salves for the topical treatment of human and/or animal skin. Although most known salves or ointments have medicinal or soothing characteristics, they do not aid in preventing blistering or scabs and reducing or eliminating scarring of the skin tissue or have an immediate effect on the reduction of pain.

The Food and Drug Administration does not regulate many of the chemicals used in the manufacture of skincare products in today's market. This unregulated usage of toxic chemicals such as, parabens, lead, musks, formaldehyde, toluene, hydroquinone, triclosan, and phthalates, within personal skincare products has made unsuspecting consumers susceptible to harmful side effects including, but not limited to, cancer, birth defects, pregnancy complications, contact dermatitis, or hormone interruption. Thus, there is a need for the manufacture of a novel topical skin care composition that contains nontoxic preservatives, nontoxic active ingredients, and nontoxic inactive ingredients, thereby, providing a user with a safer, a more broad-spectrum, and a more and effective topical skin care composition for use to rejuvenate and heal a user's skin after a skin exfoliation treatment and/or for burn healing.

However, in view of the prior art considered as a whole at the time the present invention was made, it was not obvious to those of ordinary skill in the pertinent art how the identified needs could be fulfilled.

DESCRIPTION OF THE INVENTION

The long-standing but heretofore unfulfilled need for a topical skin care composition for healing and rejuvenation of the skin containing tetracaine, purified water, stearic acid, lauramide diethanolamine, beeswax, propylene glycol, sodium tetraborate, sodium lauryl sulfate, benzyl alcohol, glycerin, diazolidinyl urea, triethanolamine, methyl salicylate, and *eucalyptus* oil. The topical skin care composition of the invention is useful in the healing of the skin and in particular, after the skin has been exfoliated. The novel topical moisturizing formulation also includes improvements that overcome the limitations of prior art topical skin care compositions and is now met by a new, useful, and non-obvious invention.

The following description is not to be construed as limiting. Numerous specific details are described to provide a thorough understanding of the invention. However, in certain instances, well know or conventional details are not described in order to avoid obscuring the description. References to one or an embodiment in the present disclosure are not necessarily references to the same embodiment; and, such references refer to at least one.

Reference in this specification to "a general embodiment" or "an alternate embodiment" means that a particular feature, structure, or characteristic described in connection with the embodiment is included in at least one embodiment of the disclosure. The appearances of the phrase "an alternate embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

In a general embodiment, the novel moisturizer formulation has by weight about 0.5% to about 12% tetracaine, about 50% to about 75% water, about 5% to about 25% stearic acid, about 2% to about 7% lauramide diethanolamine, about 1% to about 5% beeswax, about 1% to about 5% propylene glycol, about 0.2% to about 6% sodium tetraborate, about 0.2% to about 6% sodium lauryl sulfate, about 0.2% to about 6% benzyl alcohol, about 0.2% to about 6% glycerin, about 0.1% to about 5% diazolidinyl urea, about 0.1% to about 5% triethanolamine, about 0.05% to about 3% methyl salicylate, and about 0.05% to about 3% *eucalyptus* oil.

The preferred embodiments of the present invention provide topical compositions and methods of use thereof for the alleviation of the symptoms associated with burns of human skin. The preferred embodiments of the present invention also provide a method of applying topical compositions for alleviation of the symptoms of burns with no side effects and relief from inflammation and pain normally associated with burns while preventing or reducing scabbing and/or scarring of the skin. The surfactant and the anesthetic are formulated together in a pharmaceutically acceptable topical carrier, which may take any of a number of acceptable forms. Suitable carriers include aqueous carriers and oleaginous carriers. The composition may contain one or more additional agents, including antimicrobial agents, anti-viral agents, anti-fungal agents, buffering agents, antioxidants, preservatives, coloring agents, fragrances, lubricants, moisturizers, sunscreens, drying agents and the like and, more specifically, may include ingredients such as stearic acid, lauramide DEA, borax, *eucalyptus* oil, beeswax, preservative and methylparaben.

The composition can also contain antimicrobials, including antibiotics, antifungals, and other anti-viral compounds, which may complement or supplement the activity of the basic composition. Suitable antibiotics include tetracycline, polymyxin B or other common antibiotics used in topical compositions, especially over-the-counter formulations. Examples of useful antifungals include tolnaftate and micatin. Examples of antivirals include interferon, either natural or recombinant, as well as nucleoside analogs, e.g., Acyclovir. Counter-irritants such as camphor and menthol, drying agents such as benzyl alcohol, resorcinol and phenol, and astringents such as zinc sulfate and tannic acid can also be added to the composition as can other types of agents such as sunscreens, emollients, preservatives, fragrances, antioxidants, color additives, lubricants, moisturizers or drying agents. For example, a sunscreen, e.g., PABA, can be added to the formula since it is known that cold sores can be triggered by ultraviolet radiation.

The composition can be prepared in almost any relatively inert topical carrier. Generally, the formulation could take several forms, e.g., cream, gel, ointment, "Chapstick" and solution forms. Each of these formulations may contain the two active ingredients as well as microorganism growth inhibitors (preservatives). Many such carriers are routinely used and can be obtained by reference to pharmaceutical texts. Examples include polyethylene glycols (PEG), polypropylene copolymers (Pluronics), and some water-soluble gels. The preferred carrier is an emulsified cream, but other common carriers such as certain petrolatum or mineral oil-based ointments in which the surfactant and anesthetic are dispersible can be substituted.

The preferred embodiments of the present invention provide a topical composition for reducing the symptoms of burns and shortening time required for healing. The composition preferably comprises a therapeutically effective amount of a combination of an anesthetic and a surfactant. Varying amounts of anesthetic, such as tetracaine, are preferably used to achieve efficacious results, e.g., for anesthetic concentrations of from about 0.05% to about 25% by weight, preferably 0.25% to 10% by weight, and most preferably 0.5% to 12% by weight. In particular, although the low value of about 0.05% by weight of tetracaine may include, but not be limited to, ophthalmic use levels and/or may be ineffective and far below the minimum required by the FDA. The higher value of about 25% by weight of tetracaine may include, but not be limited to, new drug applications approaching a toxic level for experimental treatments and may be toxic and forbidden by the FDA. A range between 0.5% and 12% by weight of tetracaine is based on the FDA's approved levels of tetracaine for ophthalmic and topical products to be effective and non-toxic when treating the target condition.

In preferred embodiments, the anesthetic is preferably selected from the group consisting of esters, amides, ethers, and combinations thereof and, in particular, topical anesthetics and other anesthetics which may be formulated in accordance with the preferred embodiments of the present invention and applied topically, including procaine, chloroprocaine, tetracaine, propoxycaine, benzocaine, cocaine, proparacaine, bupivacaine, dibucaine, etidocaine, lidocaine, mepivacaine, prilocaine, dyclonine, promazine and combinations thereof.

The novel topical skin care composition may also contain one or more additional agents, including antimicrobial agents, anti-viral agents, anti-fungal agents, buffering agents, antioxidants, preservatives, coloring agents, fragrances, lubricants, moisturizers, sunscreens, drying agents and the like and, more specifically, may include ingredients such as stearic acid, lauramide DEA, borax, *eucalyptus* oil, beeswax, preservative and methylparaben.

The preferred embodiments of the present invention also provide a method for reducing the symptoms of burns including swelling, redness, pain, and scarring while also decreasing time required for healing by topically administering a composition according to a preferred embodiment of the present invention to a burn area, preferably at least about once every twelve hours and, more preferably, about every four hours depending upon the amount of pain. The composition is preferably applied to the burn area daily for maximum benefit. Relief is almost immediate, and is characterized by decreased pain, swelling, and more rapid healing as compared with untreated burns. In addition, the topical administration of the composition reduces or prevents scabbing and scarring of the skin affected by the burn.

It is within the scope of this invention for the novel topical skin care composition to include by weight about 50% to about 75% purified water.

In a preferred embodiment, the novel topical skin care composition has by weight about 5% to about 25% stearic acid. Stearic acid is a surfactant capable of lowering the surface tension of oils to allow water to combine with dirt, sweat and excess sebum from the skin and hair to help wash them away. It is also within the scope of this invention for stearic acid to be a high temperature emulsifier.

In a preferred embodiment, the novel topical skin care composition has by weight about 2% to about 7% lauramide diethanolamine. Lauramide diethanolamine is a fatty acid derivative of diethanolamine and is capable of increasing foaming capacity and thickening the aqueous water portion of the novel moisturizer formulation. It is also within the scope of this invention for lauramide diethanolamine to be an emulsifier and a texture modifier.

In a preferred embodiment, the novel topical skin care composition has by weight about 1% to about 5% beeswax. It is within the scope of this invention for beeswax to be a natural emulsifier and a skin conditioner.

In a preferred embodiment, the novel topical skin care composition has by weight about 1% to about 5% propylene glycol. It is within the scope of this invention for propylene glycol to be a texture modifier and a solvent. In particular, propylene glycol is an organic, colorless, and odorless synthetic liquid capable of absorbing water. It is known to function as a humectant, a solvent, an emollient, and/or a preservative in skincare products in today's market. Propylene glycol is characterized by its hydrating properties and is often a delivery ingredient, whereby, retaining moisture on the skin to facilitate absorption of potent ingredients into the skin.

In a preferred embodiment, the novel topical skin care composition has by weight about 0.2 to about 6% sodium tetraborate. Borates such as borax or sodium tetraborate decahydrate are used in the production of skin creams due to their desirable moisture retention properties. Borax also has emulsifying properties that improve the consistency of cosmetic creams and lotions.

In a preferred embodiment, the novel topical skin care composition has by weight about 0.2% to about 6% sodium lauryl sulfate. Varying amounts of surfactant are preferably used to achieve efficacious results, e.g., for surfactant, concentrations of from about 0.05% to 50% by weight, 1% to 10% by weight, and 0.2% to 6% by weight. It is within the scope of this invention for sodium lauryl sulfate to be a detergent, a surfactant, and/or a stabilizer. In an alternate embodiment, the surfactant is may be selected from the group consisting of anionic, nonionic, and cationic surfactants and combinations thereof. Suitable ionic surfactants include anionic surfactants such as monovalent salts, e.g., sodium and potassium salts of alkyl, aryl and alkyl-aryl sulfates and sulfonates, particularly those with from about 8 to 22 carbon atoms, and cationic surfactants, such as quaternary ammonium salts. Suitable non-ionic surfactants include polyethylene oxide adducts of fatty alcohols, e.g., alkylated polyoxyethylenes, alkylated polyoxyethylene-polyoxypropylene copolymers, and the surfactant nonoxynol. The surfactant and the anesthetic are preferably formulated together in a pharmaceutically acceptable topical carrier, which may comprise one of a number of known acceptable forms. Suitable topical carriers include known aqueous carriers and oleaginous carriers.

In a preferred embodiment, the novel topical skin care composition has by weight about 0.2% to about 6% benzyl alcohol. It is within the scope of the current invention for the novel topical moisturizer formulation to have at least one broad spectrum preservative. Benzyl alcohol inhibits growth of microbes including, but not limited to, bacteria, mold, yeast, and fungus within the novel topical moisturizer formulation.

In a preferred embodiment, the novel topical skin care composition has by weight about 0.2% to about 6% glycerin. It is within the scope of the current invention glycerin to be a humectant and a texture modifier.

In a preferred embodiment, the novel topical skin care composition has by weight about 0.1% to about 5% diazolidinyl urea. It is within the scope of the current invention for diazolidinyl urea to be an anti-microbial narrow-spectrum preservative capable of inhibiting growth of microbes including, but not limited to, bacteria, mold, yeast, and fungus within the novel topical moisturizer formulation.

In a preferred embodiment, the novel topical skin care composition has by weight about 0.1% to about 5% triethanolamine. It is within the scope of the current invention for triethanolamine to be a pH buffer and stabilizer. In particular, triethanolamine is used to make the novel topical skin care composition more stable and to improve texture.

In a preferred embodiment, the novel topical skin care composition has by weight about 0.05% to about 3% methyl salicylate. It is within the scope of the current invention for methyl salicylate to have analgesic properties. In particular, methyl salicylate is used to make the novel topical skin care composition to relieve pain to the skin. Methyl salicylate can be used as an anti-inflammatory agent in topical pain relief creams for muscles and joints. Many over-the-counter products contain methylsalicylate because of its mild analgesic and anti-inflammatory properties. However, the incorporation of methyl salicylate within this novel topical skin care composition will relieve an individual of pain associated with for example, post-exfoliated skin burns.

In a preferred embodiment, the novel topical skin care composition has by weight about 0.05% to about 3% plant extract. It is within the scope of this invention for the plant extract to include, but not be limited to, *papaya* extract or *eucalyptus* oil. In a preferred embodiment, the plant extract has been manipulated by at least one process to produce a preservative free and most optimal biocompatibility with the skin of a user. At least one process the plant extract may undergo includes, but is not limited to, zeodration drying process, titration using high performance liquid chromatography, and the addition of glycerin. It is within the scope of this invention for about 0.05% to about 3% *Eucalyptus* oil to be included in the novel topical skin care composition. *Eucalyptus* oil is classified as an essential oil derived from the leaves of *eucalyptus* trees. *Eucalyptus* oil is characterized by its antibacterial, anti-inflammatory and pain-killing qualities, whereby, this oil is used medicinally for analgesic, anticatarrhal, expectorant, antispasmodic, insecticidal and antiviral applications.

The novel topical skin care composition may be retained in an air tight vessel including, but not limited to, a bottle, a jar, a bag, a syringe, a container having a roller ball applicator, or an airless pump syringe. It is within the scope of this invention for the air tight vessel to be any sterile dispenser capable of retaining the novel topical skin care composition. A preferred embodiment of the sterile dispenser is an airless pump bottle or an airless pump syringe capable of protecting the novel topical moisturizer formulation by preventing excessive exposure to air and preventing exposure to a user's cross contamination, thus increasing product shelf life and protecting the formulation from harmful microorganisms associated with cross contamination by a user. The airless bottle or the airless syringe has no dip tube but rather a diaphragm that rises to evacuate the product, thus, a user does not come into contact with the entire reservoir retaining the novel topical moisturizer formulation. When user depresses the pump, it creates a vacuum effect, drawing the product upwards. A user can use almost all of the products without any waste left over and the problem of standard pumps not working appropriately is eliminated.

The invention claimed is:

1. A formulation, comprising, by weight:
   about 0.5% to about 12% tetracaine;
   about 50% to about 75% water;
   about 5% to about 25% stearic acid;
   about 2% to about 7% lauramide diethanolamine;
   about 1% to about 5% beeswax;
   about 1% to about 5% propylene glycol;
   about 0.2% to about 6% sodium tetraborate;
   about 0.2% to about 6% sodium lauryl sulfate;
   about 0.2% to about 6% benzyl alcohol;
   about 0.2% to about 6% glycerin;
   about 0.1% to about 5% diazolidinyl urea; and,
   about 0.05% to about 3% *eucalyptus* oil.

2. The formulation of claim 1, wherein the formulation having by weight about 0.1% to about 5% triethanolamine.

3. The formulation of claim 2, wherein the formulation having by weight about 0.05% to about 3% methyl salicylate.

4. The formulation of claim 1, wherein the formulation having by weight about 0.05% to about 3% methyl salicylate.

5. A formulation, comprising, by weight:
   about 0.5% to about 12% tetracaine;
   about 50% to about 75% water;
   about 5% to about 25% stearic acid;
   about 2% to about 7% lauramide diethanolamine;

about 1% to about 5% beeswax;
about 1% to about 5% propylene glycol;
about 0.2% to about 6% sodium tetraborate;
about 0.2% to about 6% sodium lauryl sulfate;
about 0.2% to about 6% benzyl alcohol;
about 0.2% to about 6% glycerin;
about 0.1% to about 5% triethanolamine; and,
about 0.05% to about 3% *eucalyptus* oil.

6. The formulation of claim 5, wherein the formulation having by weight about 0.05% to about 3% methyl salicylate.

7. A formulation, comprising, by weight:
about 0.5% to about 12% tetracaine;
about 50% to about 75% water;
about 5% to about 25% stearic acid;
about 2% to about 7% lauramide diethanolamine;
about 1% to about 5% beeswax;
about 1% to about 5% propylene glycol;
about 0.2% to about 6% sodium tetraborate;
about 0.2% to about 6% sodium lauryl sulfate;
about 0.2% to about 6% benzyl alcohol;
about 0.2% to about 6% glycerin;
about 0.05% to about 3% methyl salicylate; and,
about 0.05% to about 3% *eucalyptus* oil.

* * * * *